(12) United States Patent  
Lundberg et al.

(10) Patent No.: US 8,137,278 B2  
(45) Date of Patent: Mar. 20, 2012

(54) SYSTEM AND METHOD FOR SPATIAL COMPOUNDING USING PHASED ARRAYS

(75) Inventors: Andrew K. Lundberg, Woodinville, WA (US); Mitchell Kaplan, Lake Forest Park, WA (US); Robert E. Stone, Seattle, WA (US); Ramachandra Pailoor, Woodinville, WA (US); Clinton T. Siedenburg, Everett, WA (US); Zuhua Mao, Issaquah, WA (US)

(73) Assignee: Sonosite, Inc., Bothell, WA (US)

( * ) Notice: Subject to any disclaimer, the term of this patent is extended or adjusted under 35 U.S.C. 154(b) by 913 days.

(21) Appl. No.: 11/854,373

(22) Filed: Sep. 12, 2007

(65) Prior Publication Data

US 2009/0069681 A1    Mar. 12, 2009

(51) Int. Cl.  
*A61B 8/00*    (2006.01)

(52) U.S. Cl. ........................... 600/443; 600/447

(58) Field of Classification Search ................ 600/443  
See application file for complete search history.

(56) References Cited

U.S. PATENT DOCUMENTS

| | | | |
|---|---|---|---|
| 5,261,408 A | 11/1993 | Maslak et al. | |
| 6,390,981 B1 * | 5/2002 | Jago | 600/443 |
| 6,708,055 B2 | 3/2004 | Geiser et al. | |
| 6,790,181 B2 * | 9/2004 | Cai et al. | 600/443 |

FOREIGN PATENT DOCUMENTS

EP    1903353 A1    3/2008

OTHER PUBLICATIONS

Von Ramm et al., Beam Steering with Linear Arrays, Aug. 1983, IEEE Transactions on Biomedical Engineering, vol. BME-30, No. 8.*  
International Search Report issued for PCT/US2008/075367 dated Nov. 14, 2008, 9 pgs.  
Carr, Jonathan, "Surface Reconstructing in 3D Medical Imaging", Department of Electrical Engineering, University of Canterbury, Christchurch, New Zealand, Feb. 1996, 213 pgs.  
Supplementary European Search Report issued Feb. 15, 2011 in European Application No. 08830904.2, 7 pages.

* cited by examiner

*Primary Examiner* — Long V. Le  
*Assistant Examiner* — Nicholas Evoy  
(74) *Attorney, Agent, or Firm* — Fenwick & West, LLP

(57) ABSTRACT

The present invention is directed to a system and method which makes a phased array look like a curved array for purposes of performing spatial compounding calculations. In one embodiment, the phased array is treated as though it were a curved array by creating both a virtual apex and a virtual radius of curvature. Based on this transformation, standard spatial-compounding resampling tables can be used just as they are with curved arrays. In one embodiment, after the data is compounded to form the target image, certain data is removed prior to the actual display. This removed data represents data generated by virtual rays the prior to the physical skin line of the phased array.

25 Claims, 5 Drawing Sheets

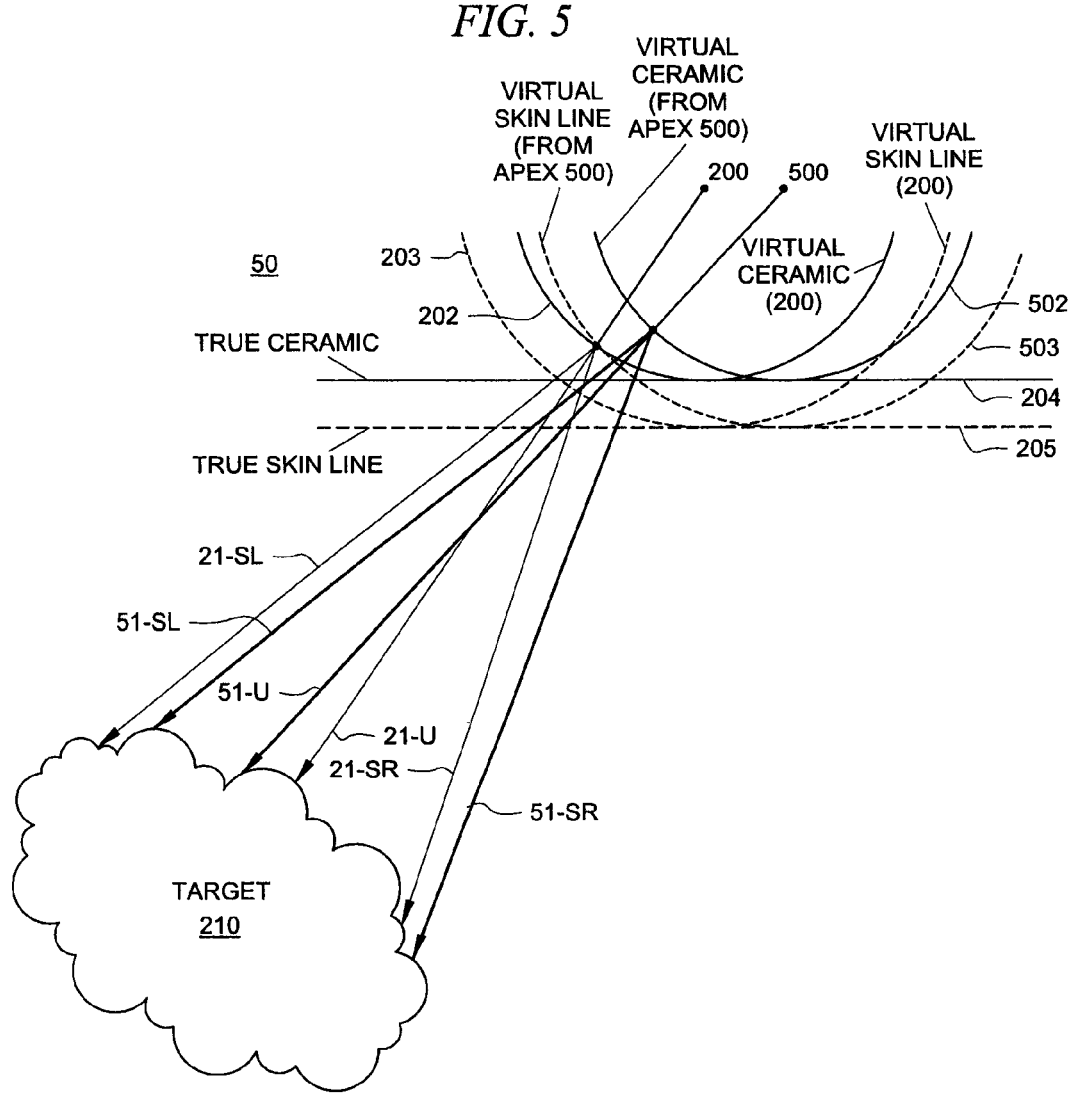

SYSTEM AND METHOD FOR SPATIAL COMPOUNDING USING PHASED ARRAYS

CROSS-REFERENCE TO RELATED APPLICATIONS

The present application is related to U.S. patent application Ser. No. 11/749,319 filed May 16, 2007 entitled "SYSTEM AND METHOD FOR OPTIMIZED SPATIO-TEMPORAL SAMPLING," the disclosure of which is incorporated by reference herein.

TECHNICAL FIELD

This disclosure relates to ultrasound imaging and more particularly to systems and methods for spatial compounding using linear arrays and even more specifically to phased arrays.

BACKGROUND OF THE INVENTION

Spatial compounding is a method of creating an ultrasound image by compiling multiple views acquired at different angles. Each view is obtained from multiple lines of sight at different angles. This is a departure from traditional ultrasound imaging that used a single line of sight perpendicular to the scanhead face. The views from the multiple angles are combined to create a single image, thereby reinforcing real-tissue information and suppressing random artifacts. Spatial compounding has resulted in a reduction in speckle noise artifacts; shadowing artifacts and image-degrading artifacts. In addition, such compounding, which is also known as compound imaging, results in improvements in: contrast resolution; needle visualization; tissue contrast resolution; fine-structure delineation; interface/border continuity and lateral edge detection.

The original literature called this technique Compound Imaging. Many companies are now using this technique, calling it various names including: SonoCT; CrossBeam Imaging; and Spatial Compounding.

Some systems use a method where information from both the transmit and the receive beam steering is processed to produce images from multiple view angles. The multiple images are aligned and combined to form an image. Images that are created using both transmit and receive information are typically superior to images consisting of receive information only.

One system for generating sonographic images is to use phased arrays, which, for example, can have 64, 128 (or if desired, any other number) elements. In phased arrays, all of the array elements (64 or 128) must be selectively pulsed to form the wavefront for each scan line. Each scan line has its own unique angle with respect to the transducer face in the sector format. Thus, the geometry of each ray is independent of the geometry from other rays. Electronic focusing is required for both transmitting energy into the subject as well as for receiving the energy reflected back from the target. A phased array typically has a linear geometry, but the shape of the images produced are usually sectors similar to those produced by curved arrays.

As part of the compounding process, image data corresponding to the different views must be resampled, or geometrically aligned to a common set of coordinates, before they are combined. For curved arrays, the symmetry of the beams (i.e, they are equally spaced in angle) simplifies this process because the tables required to perform the resampling are identical for each beam, except for a simple translation. In general, spatial compounding for phased arrays is much more complicated because the beams are typically not equally spaced. Since, as described above, each ray has a unique geometry, the resampling of each ray is also unique to that ray. Thus, because the rays lack symmetry, each beam requires a unique table for registration. Therefore, a very large amount of computation and/or very large tables are required to register the image data from the different views.

BRIEF SUMMARY OF THE INVENTION

The present invention is directed to a system and method which makes a phased array look like a curved array for purposes of performing spatial compounding calculations. In one embodiment, the phased array is treated as though it were a curved array by creating both a virtual apex and a virtual radius of curvature. Based on this transformation, standard spatial-compounding resampling tables can be used just as they are with curved arrays. In one embodiment, after the data is compounded to form the target image, certain data is removed prior to the actual display. This removed data represents data generated by virtual prior to the physical skin line of the phased array.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 5 shows one alternative embodiment.

DETAILED DESCRIPTION OF THE INVENTION

Figure 1:
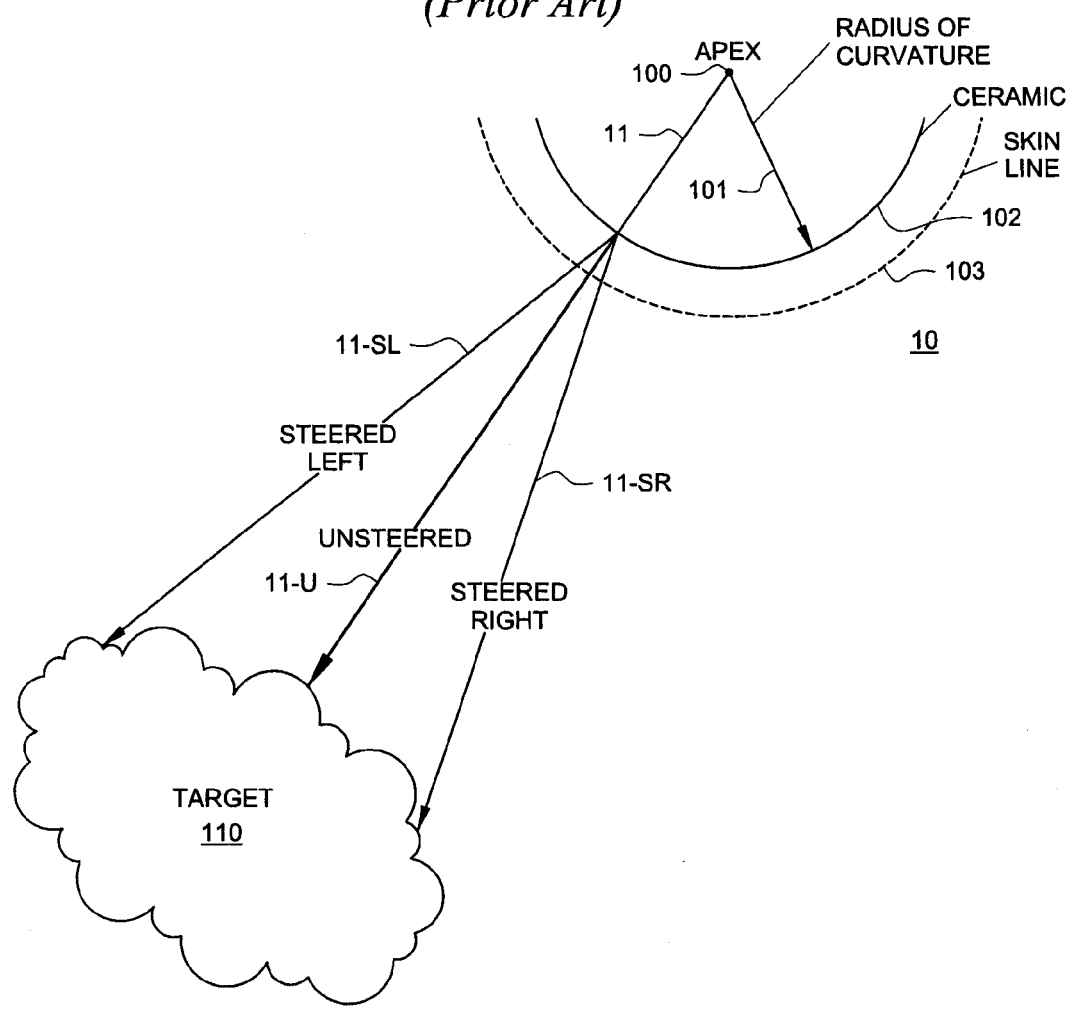
FIG. 1 shows one schematic illustration of an embodiment of a the operational theory of image generation using a curved array in accordance with the prior art.

FIG. 1 shows one schematic illustration 10 of an embodiment of a the operational theory of image generation using a curved array in accordance with the prior art. FIG. 1 shows one method for spatially compounding beams formed along a curved array. This technique is well-known in the art and can be accomplished, for example, using concepts discussed in the above-identified U.S. patent application Ser. No. 11/749, 319.

Curved array 102 has apex 100 and radius of curvature 101. Unsteered ray 11, emanating from apex 100 is perpendicular to the array surface, which in one embodiment can be ceramic. This ray (also called a beam) is steered left (11SL) and steered right (11SR) as discussed in the P35 application to paint the target, such as target 110 below skin line 103 of the subject. This trio of beams (as well as many others as are desired) can be moved anywhere along aperture 102 to form the different look directions that need to be acquired for spatial compounding.

The beam can be moved anywhere that is perpendicular to surface 102 of the scan head and the resampling computations are identical for beams at any one of those locations. This then results in a minimal amount of information that must be stored in order to resample properly formed beam data for subsequent conversion into pixel images for display to a user. Once resampled, the data from the various steered rays can be combined and scan-converted to produce spatial compounded images.

Figure 2:
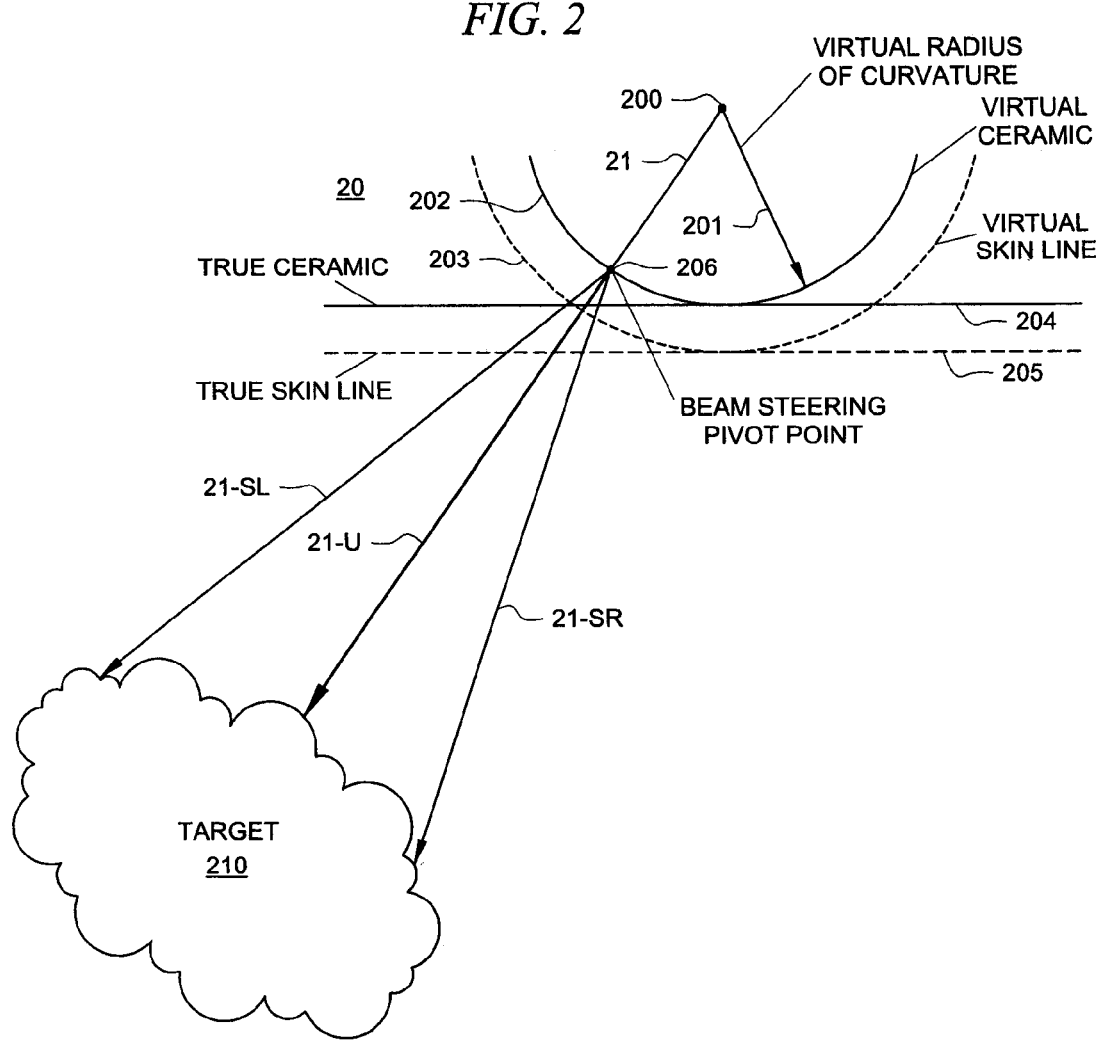
FIG. 2 shows one schematic illustration of an embodiment of a the operational theory of image generation using a phased array in accordance with one aspect of the invention.

FIG. 2 shows one schematic illustration 20 of an embodiment of the operational theory of image generation using a phased array in accordance with one aspect of the invention. As shown, rays from the surface (scan head) of a phased array, such as from scan head 204, which typically has elements arranged along a line, are mathematically calculated as if they emanate from apex 200. Thus apex 200 becomes a virtual apex having virtual radius of curvature 201 with virtual scan head 202 and virtual skin line 203.

Then, by using the same concepts as performed by curved arrays (as discussed with respect to FIG. 1), a beam, such as beam 21 can be constructed that is perpendicular to virtual surface 202. Beam 21 can be steered left (21SL) and steered right (21SR) to focus on all or a part of target 210 which is located within a subject below actual skin line 205 which is displaced from actual scan head 204 by the thickness of the lens. Note that beam steering pivot point 206 and virtual radius of curvature need not coincide with virtual ceramic 202 used for beamforming, and also note that the virtual skin line need not be tangent to the actual skin line.

Thus the phased array is leveraged off of the calculations made for curved arrays since the different look directions are not tied to the physical ceramic structure of the phased array scan head. A modification that must be made to use phased arrays in this manner is to take into account that while a virtual apex and radius is being used, the ultrasound beam emanates from the true skin line rather than from the virtual skin line. Thus, the data acquired corresponding to the region between the virtual skin line and true skin line is meaningless and is not displayed. The symmetry of the virtual curved array construct avoids requiring unique resampling tables for each beam; a single table is used for all beams. Without this, time-consuming calculations and/or very large tables would be required Rays 21U, 21SL and 21SR are the rays the system uses for imaging the target. As noted above, while only three such lines are shown, any number of rays can be used. These rays represent the center of the beam and only data coming from those portions of the respective beams that are below the actual skin line (within the subject) are used for the ultimate image presentation. However, since the calculation for compounding of the various rays is made before the virtual data is removed, the calculations are easier and faster to make thereby allowing a linear array, such as a phased array, to be used for quickly moving targets such as for cardiac imaging applications.

Figure 3:
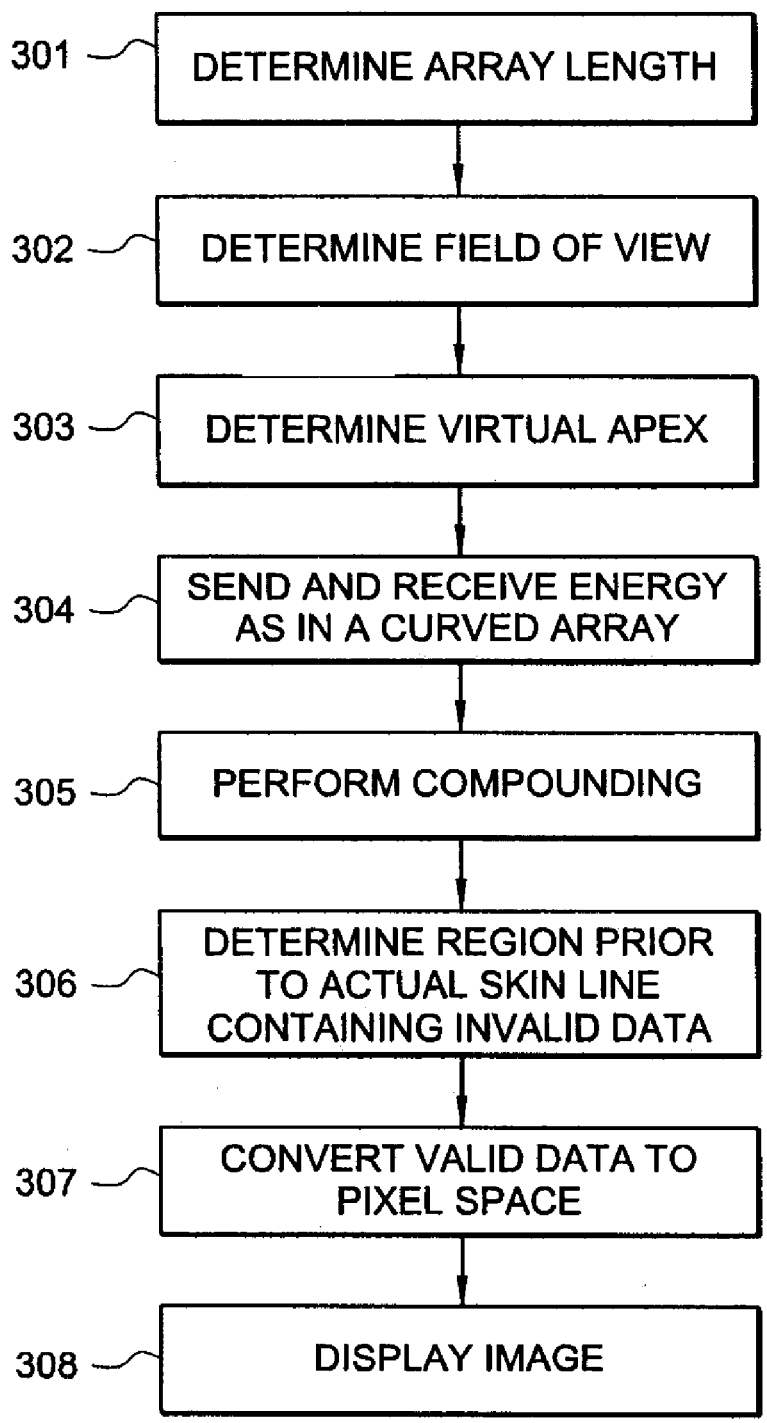
FIG. 3 shows one embodiment of a method for constructing a virtual apex and employing the concepts herein.

FIG. 3 shows one embodiment 30 of a method for constructing a virtual apex 303 given the length of the phased array 301 and the desired field of view 302. The virtual apex determines the virtual radius. Note that, as will be discussed, more than one virtual apex can be used, if desired, or the virtual scanhead properties could be computed to meet different requirements.

Process 304 transmits energy along rays to the target within the subject and receives energy along rays back as in a curved array. The calculated virtual radius of curvature has been substituted for the actual radius of curvature of the curved array.

Process 305 performs compounding, such as spatial compounding, on the received rays as is done with the curved arrays using the fact that the tables required to register the steered and unsteered beam data are the same for all rays.

Process 306 then removes the virtual data by, for example, by discarding the data acquired prior to the actual skin line. In this context, "prior to skin line" means data that is collected earlier in time than is data from the signal as it enters the skin line. In order to mimic the curved array, data is recorded that would correspond to times before the ultrasound beam is emitted from the scanhead. This is required to make the phased array look like a curved array, but it means that the data (i.e., the data collected prior to the skin line) is not valid and should not be displayed. The data to be removed depends upon timing and necessarily on scanhead orientation. The system knows which data to discard from the geometry of the problem. This can be a look-up in a table, if desired. Note that while the data to be discarded is carried along for calculation purposes (so that the problem being solved is the same as for a curved array), it is removed at the end of the process.

Process 307 converts the remaining compounded data to pixel space. Process 308 then displays the pixel space data as an image on a screen or other read-out mechanism.

For quickly moving objects, concepts herein and in the above-identified patent application greatly facilitates the display of a clear image using a phased array. In one embodiment, the number of transmit rays used is the same as in a conventional non-compounded frame, but they are divided among two or more different views for compounding. The multi-look acquisition realizes the benefits of spatial compounding and effectively restores the line density close to that of the original non-compounded frame, thus avoiding undersampling artifacts that might otherwise arise from the use of fewer transmit rays.

Figure 4:
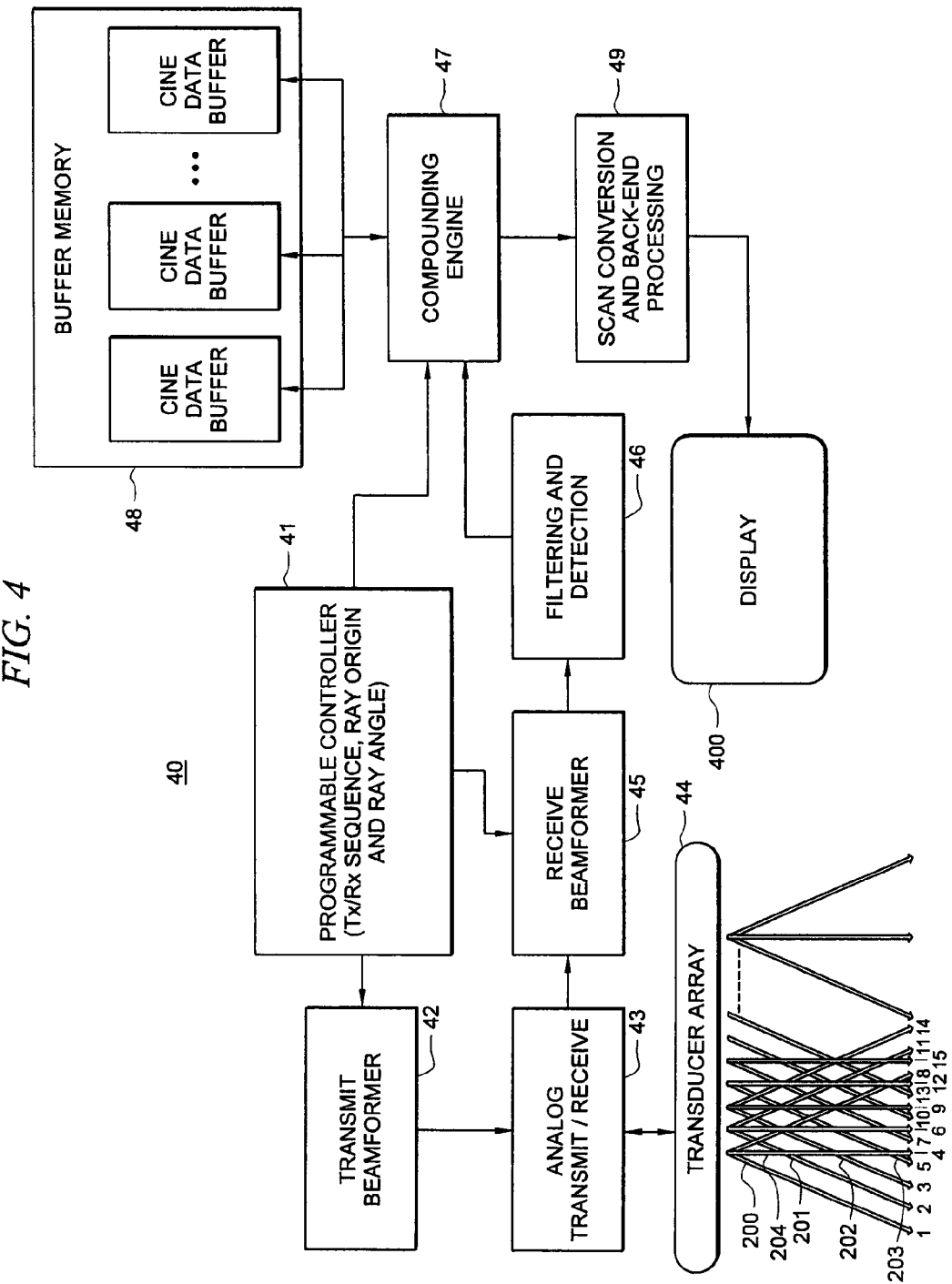
FIG. 4 shows one embodiment of a sonographic system that can employ the concepts discussed herein.

FIG. 4 shows one embodiment 40 of an implementation of the concepts discussed herein. Controller 41 generates the transmit sequence as well as the steerage angle for the beams in conjunction with beamformer 42 and analog transmitter/receiver 43. Controller 41 can comprise, for example, one or more processors that perform the ray angle adjustment or the ordinate location control for the respective rays of each time frame. The output of transmitter/receiver 43 supplies the transmit signals to transducer array 44. Transducer 44 receives a sequence of rays reflected from a subject which are used to form an image.

In the example, there are 128 rays for each steer angle (the rays are numbered in an example firing sequence using three steers) in each time differentiated frame. The returned signal for each fired ray is received by array 44 and communicated via analog transmitter/receiver 43 to receive beamformer 45. The output of the receive beamformer is a digitally sampled and beamformed ray. This ray is then filtered and detected by component 46 and sent to compounding engine 47 for compounding. Each collection of similarly steered rays are resampled (aligned), scan converted into a common grid and buffered by the compounding engine and stored in buffer memory 48. When enough data is present to compound (or combine) the data from different steers, the compounding engine computes a weighted average for each common sample in the buffer memory for the given frame of ultrasound data. The compounded data is then sent from the compounding engine to the scan converter 49 for processing for display 400.

The procedures used herein can be focused on a "region of interest," one of which is the middle of the screen. Also note that the looping example is one implementation and other loop orders can be used as well as reverse order loops and the addition of additional loops to cover additional steer directions. Note also that in the context of the discussion herein steered straight need not be perfectly straight but could have some distortion thereto in the order of, say, five degrees. Also, the ray called "straight" need not be used if desired.

FIG. 5 shows one alternative embodiment 30 in which more than one virtual apex is created. Multiple virtual apices may be used instead of or in conjunction with multiple steer angles for compounding. That is, different views for spatial compounding may be obtained by steering rays at different angles, by employing rays with different virtual apices, or both, as desired. Thus, as shown, virtual apex 500 has virtual ceramic 502 and virtual skin line 503. Virtual skin line 503 is not tangent to actual skin line 205 of the subject. Note also that the virtual ceramics 202 and 502 need not touch and thus rays 510 and 210 need not intersect at a common point of the respective virtual ceramic lines.

It should be noted that the embodiments discussed herein are just one example of the use of the concepts described. For example, compounding of the beams can occur after scan conversion to pixel space, if desired. Also, it is possible to acquire an entire frame along a single look direction before acquiring data along another look direction and then compounding the looks.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of performing spatial compounding using a sonographic phased array comprising:
   with a sonographic phased array, simulating at least one virtual apex and at least one virtual radius of curvature corresponding to a virtual curved array;
   collecting data from transmitted and received ultrasound beams using the sonographic phased array;
   processing the collected data using curved array conceptual techniques wherein a curved array apex and radius of curvature are replaced, respectively, by the simulated virtual apex and simulated virtual radius of curvature; and
   generating image data based on processing the collected data using the simulated virtual apex and simulated virtual radius of curvature.

2. The method of claim 1 further comprising:
   discarding certain collected data pertaining to an area external to an actual skin line of the phased array.

3. The method of claim 2 wherein a virtual skin line of the virtual array is tangent to the phased array's actual skin line.

4. The method of claim 2 wherein processing the collected data comprises compounding.

5. The method of claim 4 wherein the compounding comprises spatial compounding.

6. The method of claim 5 wherein the spatial compounding occurs on beam data prior to scan-conversion.

7. The method of claim 4 wherein the certain image data is discarded after compounding and prior to display.

8. The method of claim 4 wherein the discarding comprises:
   eliminating compounded data obtained from an area external to the actual skin line.

9. The method of claim 5 wherein the spatial compounding utilizes image forming rays transmitted and/or received by the sonographic phased array the spatial compounding comprising:
   mixing the order of the rays within an image frame, and
   adjusting a sequence of particular rays to move the location of optimized temporal difference between different rays of a common frame to a desired region of interest in the subject.

10. The method of claim 2 wherein the radius is established based upon at least two of the following: form factor of the phased array, desired field of view; number of rays.

11. A system for producing sonographic image data, the system comprising:
   a scan head of a sonographic phased array configured to transmit and receive sound rays through a surface of a subject, the rays controlled in a phased array format to form a virtual apex and virtual radius of curvature corresponding to a virtual curved array; and
   a processor configured for performing compounding using curved array conceptual techniques and generating image data wherein a curved array apex and a radius of curvature are replaced, respectively, by the virtual apex and the virtual radius of curvature.

12. The system of claim 11 wherein the processor is further configured to discard compounded data pertaining to data stemming from areas prior to an actual skin line of a subject.

13. The system of claim 12 wherein a virtual skin line of the virtual curved array is tangent to the actual skin line.

14. The system of claim 13 wherein the compounding results in generation of scan data subject to pixel space conversion.

15. The system of claim 14 wherein the data is discarded prior to display.

16. The system of claim 13 wherein the compounding comprises spatial compounding.

17. The system of claim 16 wherein the spatial compounding utilizes image forming rays transmitted into and/or received from the subject, the spatial compounding comprising:
   mixing the order of the rays within an image frame, and adjusting a sequence of particular rays to move the location of optimized temporal difference between different rays of a common frame to a desired region of interest in the subject.

18. The system of claim 13 wherein the virtual radius is established based upon at least two of the following: form factor of the phased array, desired field of view; number of rays.

19. The system of claim 13 further comprising:
adjusting a ray firing sequence of particular rays within a time frame so as to move the location of optimized temporal difference between different rays of a common frame to a desired region of interest with the subject.

20. The system of claim 19 further comprising: adjusting a firing angle of at least one of the rays within the common frame.

21. The system of claim 20 wherein the adjusting comprises steering each the ray to a particular angle from normal.

22. A method of presenting images of a moving target within a subject, the method comprising:
positioning a scan head in proximity to the subject, the scan head configured to operate as a phased array, the scan head further configured to simulate a curved array by utilizing a virtual curved array, the curved array having a virtual apex and a virtual radius of curvature;
transmitting energy into the subject at a selected site location, the energy being directed as though it emanates from the virtual apex and spreads outward from a set of points along the virtual radius;
receiving reflected energy back from the moving target via the scan head; spatially compounding the reflected energy; and
plotting the compounded reflected energy into an image for presentation to a user.

23. The method of claim 22 further comprising:
discarding a portion of the spatially compounded reflected energy.

24. The method of claim 23 wherein the discarded portion is a portion represented by those portions of the transmitted energy calculated to fall external to an actual skin line of the subject.

25. The method of claim 24 wherein the virtual curved array is based upon the phase array's form factor, field of view and number of rays.

* * * * *